United States Patent [19]

Maeda et al.

[11] Patent Number: 4,780,471
[45] Date of Patent: Oct. 25, 1988

[54] FUNGICIDAL AZOLE DERIVATIVES

[75] Inventors: Takashi Maeda, Kobe; Takahiro Kataoka, Kurita; Takayuki Hatta, Koga; Masaru Ogata, Kobe, all of Japan

[73] Assignee: Shionogi & Co., Ltd., Osaka, Japan

[21] Appl. No.: 68,334

[22] Filed: Jul. 1, 1987

[30] Foreign Application Priority Data

Jul. 1, 1986 [JP] Japan ................... 61-155462

[51] Int. Cl.$^4$ .................. A01N 43/653; A01N 43/50; C07D 233/60
[52] U.S. Cl. .................... 514/383; 514/399; 548/262; 548/335; 548/341
[58] Field of Search .............. 548/341, 335, 262; 514/399, 383

[56] References Cited

U.S. PATENT DOCUMENTS

4,328,348  5/1982  Ogata et al. ................. 548/335
4,483,866  11/1984 Ogata et al. ................. 514/399

OTHER PUBLICATIONS

Chemical Abstracts, 95:115557n(1981)[Fr. Demande 2, 458,545, Ogata et al., 1/2/81].

*Primary Examiner*—Richard A. Schwartz
*Attorney, Agent, or Firm*—Wenderoth, Lind & Ponack

[57] ABSTRACT

A novel fungicidal compound of the formula:

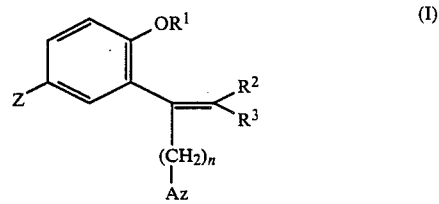

(I)

wherein $R^1$ is hydrogen, alkyl having 1 to 12 carbon atoms,

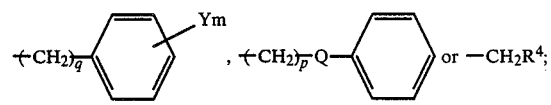

$R^2$ and $R^3$ are hydrogen, bromine or methyl; $R^4$ is alkenyl having 2 to 9 carbon atoms or alkynyl having 2 to 9 carbon atoms; m is an integer of 0 to 2; n is an integer of 0 to 1; p and q are independently integers of 1 to 8; Az is imidazolyl or 1,2,4-triazolyl, Q is —CO—, —O— or —CO—NR$^5$—; R$^5$ is hydrogen or methyl, Y is hydrogen, fluorine, chlorine or phenyl; and Z is hydrogen, fluorine, chlorine or methyl, provided that, when Z is hydrogen or chlorine, n is 1, or its salt. A process for producing the compound (I) and a fungicide containing the compound (i) are also disclosed.

3 Claims, No Drawings

FUNGICIDAL AZOLE DERIVATIVES

FIELD OF THE INVENTION

The present invention relates to novel azole derivatives, a process for producing the same and a preparation for controlling plant diseases containing the same.

BACKGROUND OF THE INVENTION

Hitherto, various azole derivatives have been proposed as agents for controlling plant diseases. For example, Japanese Patent Publication No. 60-11904 discloses a compound of the formula:

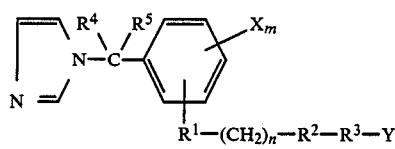

(X)

wherein m and q are independently integers of 1 to 2; n is an integer of 0 to 3; X is hydrogen or chlorine; Y is hydrogen, alkyl, methoxy, chlorine or nitro; $R^1$ is oxygen or sulfur; $R^2$ is oxygen, sulfur or methylene; $R^3$ is phenyl or thienyl; and one of $R^4$ and $R^5$ is imidazolyl and the other is phenyl, or $R^4$ and $R^5$ taken together form alkylidene, and an acid addition salt thereof. In this publication, there is described that the compound (X) is useful as an antifungal agent for human and other animals or an agricultural fungicide. Further, Japanese Patent Laid Open Publication No. 60-155163 discloses an imidazole compound of the formula:

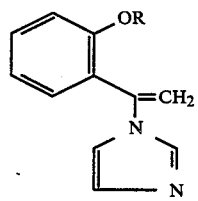

(XI)

wherein R is a straight or branched chain alkyl having 6 to 9 carbon atoms, and an acid addition salt thereof. In this laid open publication, there is described that the compound (XI) has excellent antifungal activity and is useful as an industrial fungicide which can effectively prevent the growth of various fungi in industrial materials and products.

OBJECTS OF THE INVENTION

The present inventors have studied intensively to find a fungicide which has strong activity against grey mold diseases. As a result, it has been found that a novel compound of the formula (I) shown hereinafter has remarkable antifungal activity which is different from those of the compounds disclosed in the above patent publications.

One object of the present invention is to provide a novel compound having excellent antifungal activity.

Another object of the present invention is to provide a process for producing the compound.

Still another object of the present invention is to provide a preparation for controlling plant diseases containing the compound.

These objects as well as other objects and advantages of the present invention will become apparent to those skilled in the art from the following description.

SUMMARY OF THE INVENTION

According to the present invention, there is provided a novel compound of the formula:

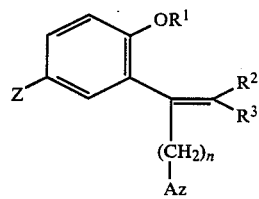

(I)

wherein $R^1$ is hydrogen, alkyl having 1 to 12 carbon atoms,

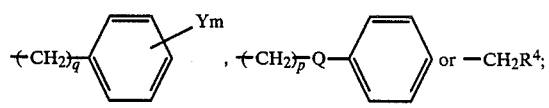

$R^2$ and $R^3$ are hydrogen, bromine or methyl; $R^4$ is alkenyl having 2 to 9 carbon atoms or alkynyl having 2 to 9 carbon atoms; m is an integer of 0 to 2; n is an integer of 0 to 1; p and q are independently integers of 1 to 8; Az is imidazolyl or 1,2,4-triazolyl, Q is —CO—, —O— or —CO—$NR^5$—; $R^5$ is hydrogen or methyl, Y is hydrogen, fluorine, chlorine or phenyl; and Z is hydrogen, fluorine, chlorine or methyl, provided that, when Z is hydrogen or chlorine, n is 1, or its salt.

The present invention also provides a process for producing the compound of the formula (I) and a preparation for controlling plant diseases which contains as an active ingredient the compound of the formula (I).

DETAILED DESCRIPTION OF THE INVENTION

In the compound of the formula (I), examples of the alkyl group having 1 to 12 carbon atoms of $R^1$ include propyl, butyl, octyl, decyl, dodecyl and the like. Examples of the alkenyl having 2 to 9 carbon atoms of $R^4$ include vinyl, propenyl, butenyl and the like, and examples of the alkynyl having 2 to 9 carbon atoms include ethynyl, butynyl, hexynyl and the like. As

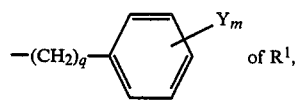

of $R^1$, there include benzyl, 3-chlorobenzyl, 4-chlorobenzyl, 2,4-dichlorobenzyl, 3,4-dichlorobenzyl, 2,6-dichlorobenzyl, 4-phenylbenzyl, phenethyl, 4-phenylbutyl, 6-phenylhexyl and the like and, as

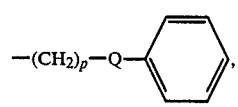

there include phenacyl, 2-phenoxyethyl, methylphenylcarbamoylmethyl and the like.

The compound (I) wherein n is 0 can be synthesized according to the processes shown in the following Schemes 1 and 2.

Scheme 1

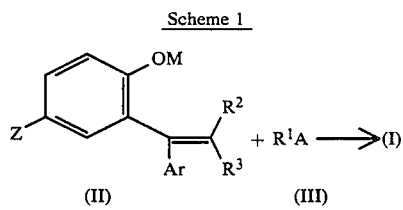

Scheme 2

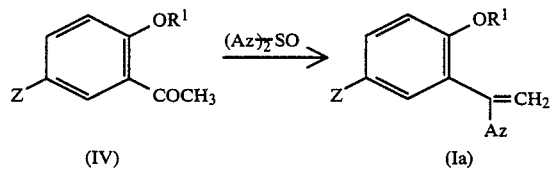

wherein M is hydrogen or alkaline metal; A is a reactive group, for example, halogen and an ester residue such as tosyloxy and $R^1$, $R^2$, $R^3$, Az and Z are as defined above.

Process of Scheme 1

The process of Scheme 1 can be carried out by reacting the phenol (II) with the reagent (III) in the presence of a base, or reacting the alkaline metal phenolate (II) with the reagent (III). Examples of the base include sodium hydroxide, sodium hydride, potassium amide, sodium ethoxide and the like. The reaction can be carried out in a suitable inert solvent, for example, dimethylformamide, benzene, methanol, chloroform, tetrahydrofuran or the like at room temperature. The phenol (II) used as the starting material is synthesized by, for example, the following reaction:

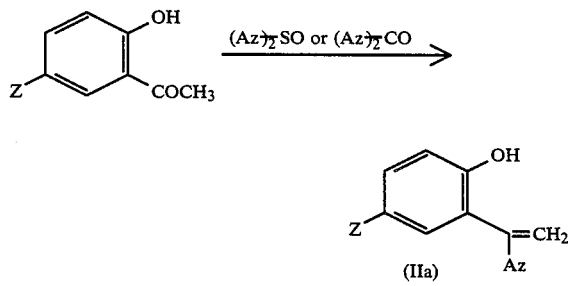

Process of Scheme 2

The process of Scheme 2 is the reaction of acetophenone (IV) with N,N'-thionyldiimidazole to effect addition of imidazole and dehydration simultaneously or sequentially to form the ethylene (Ia). The reaction is carried out in a suitable solvent at room temperature, or with cooling or heating. As the solvent, there can be used dimethyl sulfoxide, acetonitrile, dimethylformamide, methylene chloride, chloroform, 1,2-dichloroethane and the like. The acetophenone (IV) used as the starting material is obtained by the following reaction:

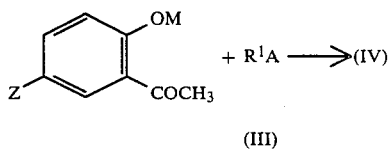

wherein $R^1$, A, M and Z are as defined above. This reaction can be carried out according to the reaction of Scheme 1.

The compound (I) wherein n is 1 can be synthesized by the processes shown in the following Schemes 3 to 5:

Scheme 3

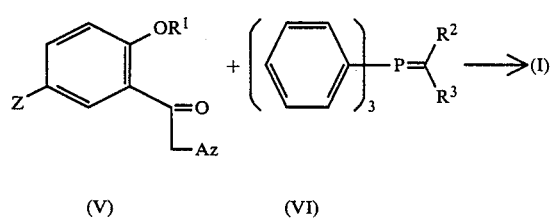

Scheme 4

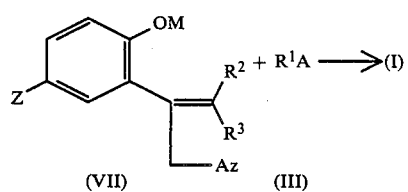

Scheme 5

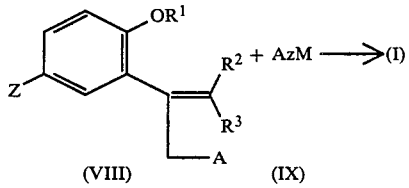

wherein M is hydrogen or alkaline metal; A is a reactive group, for example, halogen and an ester residue such as tosyloxy and $R^1$, $R^2$, $R^3$, Az and Z are as defined above.

Process of Scheme 3

The process of Scheme 3 can be carried out by reacting the ketone (V) with the alkylidene phosphorane (VI). This reaction can be carried out in a suitable inert solvent, for example, dimethyl sulfoxide, diethyl ether, dioxane, tetrahydrofuran, or benzene at room temperature to 150° C. The ketone (V) used as the starting material is synthesized according to a known method as shown in the following reaction:

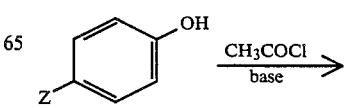

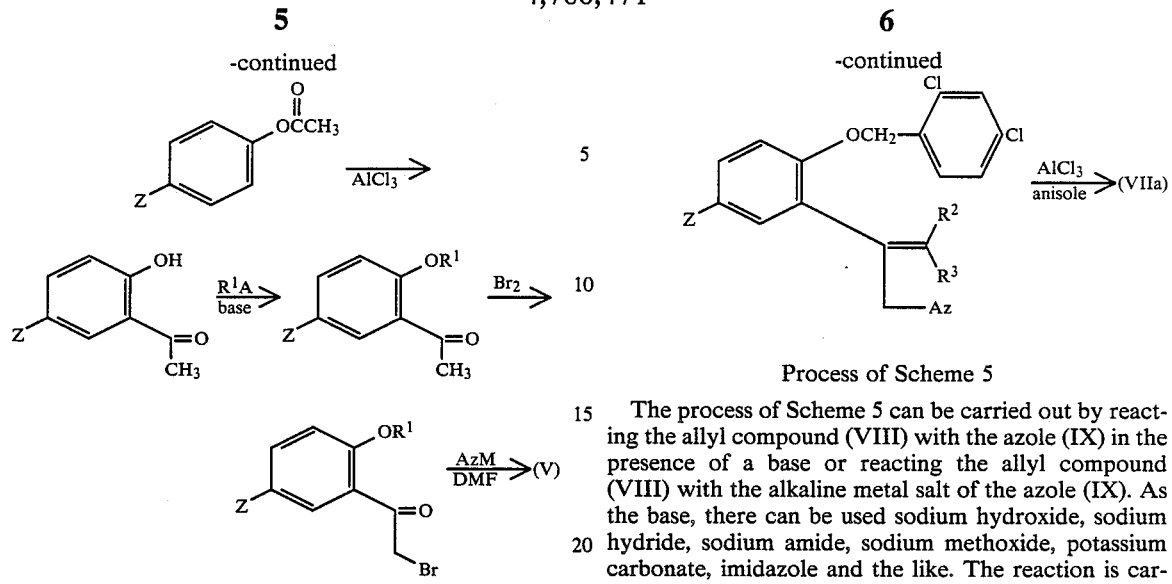

The alkylidene phosphorane reagent (VI) can be obtained by treating a phosphonium compound of the formula:

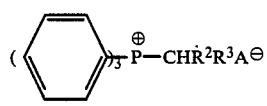

wherein A is Cl, Br or I, with a base. As the base, there can be used carbon bases such as butyl lithium, phenyl lithium, etc.; nitrogen bases such as sodium amide, lithium diethyl amide, DBU, DBN, etc.; oxygen bases such as sodium hydroxide, potassium-t-butoxide, potassium carbonate, etc.; sodium hydride and the like.

Process of Scheme 4

The process of Scheme 4 can be carried out by reacting the phenol (VII) with the reagent (III), or reacting the alkaline metal phenolate (VII) with the reagent (III). The reaction can be carried out according to the same manner as described in Scheme 1. The phenol (VII) used as the starting material is synthesized by a known method from a compound prepared according to the same manner for preparing the ketone (V) as described in Scheme 3, for example, as shown in the following reaction:

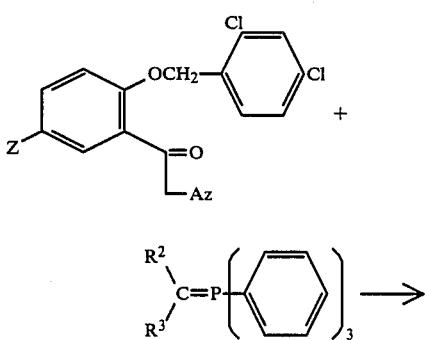

Process of Scheme 5

The process of Scheme 5 can be carried out by reacting the allyl compound (VIII) with the azole (IX) in the presence of a base or reacting the allyl compound (VIII) with the alkaline metal salt of the azole (IX). As the base, there can be used sodium hydroxide, sodium hydride, sodium amide, sodium methoxide, potassium carbonate, imidazole and the like. The reaction is carried out in an inert solvent such as dimethylformamide, dimethyl sulfoxide, benzene, chloroform, or tetrahydrofuran at room temperature to 80° C. The allyl compound (VIII) used as the starting material is synthesized by a known method from a compound prepared according to the same manner for preparing the ketone (V) as described in Scheme 3, for example, as shown in the following reaction:

The compound (I) thus obtained can be converted into a pharmaceutically acceptable acid addition salt. Examples of the salt include those formed with organic salts such as acetic acid, citric acid, tartaric acid, malic acid, succinic acid, oxalic acid, methanesulfonic acid and the like and inorganic salts such as hydrochloric acid, hydrobromic acid, sulfuric acid, nitric acid, phosphoric acid and the like.

The compound (I) or its salt of the present invention has very strong fungicidal activity and is useful for agricultural and industrial fungicides. For example, the compound (I) of the present invention shows strong fungicidal activity against plant pathogenic microorganisms such as those for grey mold diseases, sclerotia diseases, powdery mildew and the like.

The compound (I) or its salt of the present invention can be used alone or in combination with one or more solid or liquid carriers, diluents or excipients as an agricultural or gardening fungicide in the form of an emulsion, an aqueous solution, wettable powder, dust, a suspension, granules, aerosol, a fumigant, a paste and the like. Examples of solid carriers, diluents and excipients include clay, talc, diatomaceous earth, silica, kaolin, bentonite, pumice and the like. Typical examples of liquid carriers, diluents and excipients include water, methanol, ethanol, ethylene glycol, dimethylformamide, dimethyl sulfoxide, acetone, methyl ethyl ketone, cellosolve, dioxane, diglyme and the like. If necessary, there can be added suitable auxiliaries such as emulsifiers, dispersing agents, spreaders, surfactants, wetting agents, stabilizers, synergists and the like. Further, the compound (I) or its salt of the present invention can be used in combination with other agricultural medicnes such as other fungicides, germicides, insecticides, herbicides, repellents, acaricides, nematocides, plant growth regulators and the like.

The concentration of the active ingredient in the preparation is not limited to a specific range and varies depending upon a variety of a particular plant to be treated and its growth period. However, in the case of sprinkling the preparation to prevent or treat plant diseases, the concentration of the active ingredient is, for example, 10 to 1,000 ppm, preferably, 50 to 500 ppm.

The following Examples, Reference Examples, Experiments and Preparations further illustrate the present invention in detail but are not to be construed to limit the scope thereof.

EXAMPLE 1

1-[1-(2-Hydroxy-5-fluorophenyl)vinyl]-1H-imidazole

Thionyl chloride (17.8 g, 0.15 mole) was added dropwise over 30 minutes to 1H-imidazole (41.1 g, 0.60 mole) in dried methylene chloride (200 ml) with stirring and ice-cooling. After stirring for additional 30 minutes, 2-hydroxy-5-fluoroacetophenone (15.4 g, 0.10 mole) in dried methylene chloride (50 ml) was added dropwise over 30 minutes. After stirring for 1 hour, methylene chloride (200 ml), water (400 ml) and an aqueous saturated solution of sodium bicarbonate (200 ml) were added to the reaction mixture and the mixture was stirred for 5 minutes. Then, the organic layer was separated, washed with water and dried over anhydrous sodium sulfate. The solvent was distilled off under reduced pressure and the residue was recrystallized from ethyl acetate to obtain the title compound (3.71 g, 18.2%), m.p. 164°–166° C.

Anal. Calcd. for $C_{11}H_9FN_2O$: C, 64.47; H, 4.45; N, 13.72. Found: C, 64.47; H, 4.44; N, 13.48.

EXAMPLE 2

1-[1-[2-(2,4-Dichlorobenzyloxy)-5-fluorophenyl]vinyl]-1H-imidazole

85% Potassium hydroxide powder (36.0 g, 0.545 mole) was suspended in dimethyl sulfoxide (500 g) and stirred at 55° C. for 50 minutes. After cooling to 25° C., 1-[1-(2-hydroxy-5-fluorophenyl)vinyl]-1H-imidazole (90.0 g, 0.441 mole) was added and the mixture was stirred at room temperature for 1 hour. Then, 2,4-dichlorobenzyl chloride (94.5 g, 0.483 mole) was added dropwise over 1 hour and the mixture was stirred for 2 hours. Water (680 ml) was added dropwise over 25 minutes to the reaction mixture with stirring and then stirring was continued for additional 1 hour. The precipitated crystals were filtered off and washed with water (135 ml×5) and n-hexane (135 ml×3). The resulting crude crystals were recrystallized from n-hexane/ethyl acetate to obtain the title compound (109 g, 68.1%), m.p. 118°–120° C.

Anal. Calcd. for $C_{18}H_{13}Cl_2FN_2O$: C, 59.52; H, 3.61; N, 7.71. Found: C, 59.67; H, 3.58; N, 7.56.

EXAMPLE 3

1-[1-[2-(2,6-Dichlorobenzyloxy)-5-fluorophenyl]vinyl]-1H-imidazole

According to the same manner as in Example 2, the title compound (m.p. 108°–110° C.) was obtained except that 2,6-dichlorobenzyl chloride was used instead of 2,4-dichlorobenzyl chloride.

EXAMPLE 4

1-[1-[2-(4-Phenylbenzyloxy)-5-fluorophenyl]vinyl]-1H-imidazole

According to the same manner as in Example 2, the title compound (m.p. 97°–98° C.) was obtained except that 4-phenylbenzyl chloride was used instead of 2,4-dichlorobenzyl chloride.

EXAMPLE 5

1-[1-(2-n-Butyloxy-5-fluorophenyl)vinyl]-1H-imidazole 3/2 oxalate

According to the same manner as in Example 2, 1-[1-(2-n-butyloxy-5-fluorophenyl)vinyl]-1H-imidazole was obtained except that n-butyl bromide was used instead of 2,4-dichlorobenzyl chloride. The compound (0.74 g, 2.84 mmole) was dissolved in diethyl ether (5 ml) and a solution of oxalic acid (0.3 g, 3.33 mmole) in diethyl ether was added thereto with stirring. The solvent was distilled off under reduced pressure and the residue was recrystallized from ethyl acetate/diethyl ether to obtain the title compound (0.82 g, 73.0%), m.p. 107°–109° C.

Anal. Calcd. for $C_{15}H_{17}FN_2O.3/2C_2H_2O_4$: C, 54.67; H, 5.13; N, 7.09. Found: C, 54.68; H, 5.11; N, 7.14.

EXAMPLES 6 TO 24

According to the same manner as described above, the compounds of the present invention were prepared.

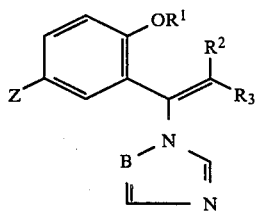

| Example No. | $R^1$ | $R^2$ | $R^3$ | Z | B | Salt | m.p. |
|---|---|---|---|---|---|---|---|
| 6 | —(CH$_2$)$_2$CH$_3$ | H | H | CH$_3$ | CH | (CO$_2$H)$_2$ | 130–132 |
| 7 | —(CH$_2$)$_2$CH$_3$ | H | H | CH$_3$ | CH | (CO$_2$H)$_2$ | 112–113 |
| 8 | —(CH$_2$)$_5$CH$_3$ | H | H | CH$_3$ | CH | (CO$_2$H)$_2$ | 113–115 |
| 9 | —(CH$_2$)$_7$CH$_3$ | H | H | CH$_3$ | CH | (CO$_2$H)$_2$ | 108–110 |
| 10 | —CH$_2$CH=CH$_2$ | H | H | CH$_3$ | CH | (CO$_2$H)$_2$ | 128.5–129.5 |
| 11 | —CH$_2$C≡CH | H | H | CH$_3$ | CH | (CO$_2$H)$_2$ | 148–149 |
| 12 | —CH$_2$C≡CH | H | H | F | CH | (CO$_2$H)$_2$ | 127– |

-continued

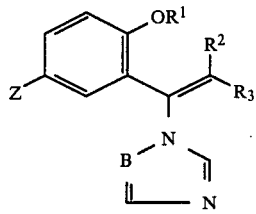

| Example No. | R¹ | R² | R³ | Z | B | Salt | m.p. |
|---|---|---|---|---|---|---|---|
| 13 | —CH₂CH=CH₂ | H | H | F | CH | (CO₂H)₂ | 129 120–121 |
| 14 | —CH₂—C₆H₅ | H | H | CH₃ | CH | HCl | 165–170 |
| 15 | —CH₂—(2-Cl-C₆H₄) | H | H | CH₃ | CH | HCl H₂O | 125–127 |
| 16 | —CH₂—(2-Cl-C₆H₄) | H | H | F | CH | — | 79–80 |
| 17 | —CH₂—(4-Cl-C₆H₄) | H | H | CH₃ | CH | — | 102.5–104 |
| 18 | —CH₂—(2,4-Cl₂-C₆H₃) | H | H | CH₃ | CH | — | 113–115 |
| 19 | —CH₂—(2,4-Cl₂-C₆H₃) | H | H | CH₃ | CH | (CO₂H)₂ | 138–139 |
| 20 | —CH₂—(2,3-Cl₂-C₆H₃) | H | H | CH₃ | CH | — | 64–66 |
| 21 | —CH₂—(2,4-Cl₂-C₆H₃) | H | H | F | CH | — | 91–93 |
| 22 | —CH₂—(2,6-Cl₂-C₆H₃) | H | H | CH₃ | CH | — | 89–90 |
| 23 | —CH₂—(2,4-Cl₂-C₆H₃) | Br | H | CH₃ | CH | (CO₂H)₂ | 119–121 |
| 24 | —CH₂—(2,4-Cl₂-C₆H₃) | H | H | CH₃ | N | — | 99–101 |

REFERENCE EXAMPLE 1

4-Fluorophenyl acetate

4-Fluorophenol (112.1 g, 1.0 mole), sodium acetate (68.89 g, 0.74 mole) and acetic anhydride (107.6 g, 1.05 mole) were mixed in benzene (220 ml) with stirring and heated under reflux for 2 hours. After cooling, water (500 ml) and sodium bicarbonate (100 g, 1.19 mole) were added to the reaction mixture and the mixture was stirred. The mixture was allowed to stand to separate into layers and the aqueous layer was extracted with benzene (500 ml). The organic layers were combined, dried over anhydrous sodium sulfate and distilled to obtain the title compound (147 g, 95.4%), b.p. 84°–86° C./16 mmHg.

REFERENCE EXAMPLE 2

2-Hydroxy-5-fluoroacetophenone

4-Fluorophenyl acetate (147 g, 0.954 mole) and anhydrous aluminum chloride (140 g, 1.05 mole) were mixed and the mixture was heated at 150° C. for 1 hour. Water (500 ml) and ice (300 g) were added to the reaction mixture simultaneously and the mixture was stirred. The precipitated crystals were filtered off and distilled under reduced pressure to obtain the title compound (86.3 g, 58.7%), b.p. 89.5°–94° C./11 mmHg (see J. Org. Chem., 16, 1345, 1348 (1951)).

EXAMPLE 25

2-[2-(2,4-Dichlorobenzyloxy)phenyl]-3-(imidazol-1-yl)-1-propene

ω-(Imidazol-1-yl)-2-(2,4-dichlorobenzyloxy)acetophenone (0.72 g, 1.99 mmole), potassium carbonate (0.36 g, 2.60 mmole) and methyltriphenylphosphonium bromide (0.79 g, 2.21 mmole) were suspended in 1,4-dioxane (15 ml) and the suspension was refluxed with stirring for 2 days. Then, the mixture was poured into water (100 ml) and extracted with diethyl ether (100 ml×2). The extract was washed with a saturated aqueous solution of sodium chloride (100 ml) and dried over anhydrous sodium sulfate. After distilled off the solvent under reduced pressure, the residue was subjected to chromatography on a silica gel column and eluted with methanol/chloroform (1:40, v/v) to obtain the title compound (0.39 g, 54.3%), m.p. 84°–86° C. (recrystallized from ethyl acetate/n-hexane).

Anal. Calcd. for $C_{19}H_{16}Cl_2N_2O$: C, 63.51; H, 4.49; N, 7.80; Cl, 19.74. Found: C, 63.44; H, 4.47; N, 7.83; Cl, 19.69

EXAMPLE 26

2-[2-(2,4-Dichlorobenzyloxy)-5-fluorophenyl]-3-(imidazol-1-yl)-1-propene

According to the same manner as in Example 25, the title compound (m.p. 79°–82° C.) was obtained except that ω-(imidazol-1-yl)-2-(2,4-dichlorobenzyloxy)-5-fluoroacetophenone was used instead of ω-(imidazol-1-yl)-2-(2,4-dichlorobenzyloxy)acetophenone.

EXAMPLE 27

2-[2-(2,6-Dichlorobenzyloxy)-5-fluorophenyl]-3-(imidazol-1-yl)-1-propene

According to the same manner as in Example 25, the title compound (m.p. 106°–108° C.) was obtained except that ω-(imidazol-1-yl)-2-(2,6-dichlorobenzyloxy)-5- fluoroacetophenone was used instead of ω-(imidazol-1-yl)-2-(2,4-dichlorobenzyloxy)acetophenone.

EXAMPLE 28

2-[2-(2,4-Dichlorobenzyloxy)phenyl]-3-(imidazol-1-yl)-1-propene oxalate

2-[2-(2,4-Dichlorobenzyloxy)phenyl]-3-(imidazol-1-yl)-1-propene (98.9 g, 0.275 mole) was dissolved in diethyl ether (200 ml) and a solution of oxalic acid (24.79 g, 0.275 mole) in diethyl ether was added thereof with stirring. The solvent was distilled off under reduced pressure and the residue was recrystallized from methanol-diethyl ether to obtain the title compound (103.5 g, 83.8%), m.p. 131°–132° C.

Anal. Calcd. for $C_{21}H_{18}Cl_2N_2O_5$: C, 56.13; H, 4.05; N, 6.28. Found: C, 55.85; H, 3.98; N, 6.08.

EXAMPLE 29

2-[2-(2,4-Dichlorobenzyloxy)phenyl]-3-(imidazol-1-yl)-1-propene hydrochloride

According to the same manner as in Example 28, the title compound (m.p. 122°–124° C.) was obtained except that hydrochloric acid was used instead of oxalic acid.

EXAMPLE 30

2-[2-(2,4-Dichlorobenzyloxy)phenyl]-3-(imidazol-1-yl)-1-propene p-toluenesulfonate According to the same manner as in Example 28, the title compound (m.p. 161°–162° C.) was obtained except that p-toluenesulfonic acid was used instead of oxalic acid.

EXAMPLE 31

2-[2-(2,4-Dichlorobenzyloxy)phenyl]-3-(imidazol-1-yl)-1-propene sulfate

According to the same manner as in Example 28, the title compound (m.p. 105°–107° C.) was obtained except that sulfuric acid was used instead of oxalic acid.

EXAMPLE 32

2-[2-(2,4-Dichlorobenzyloxy)-5-fluorophenyl]-3-(imidazol-1-yl)-1-propene oxalate According to the same manner as in Example 28, the title compound (m.p. 160°–162° C.) was obtained except that 2-[2-(2,4-dichlorobenzyloxy)-5-fluorophenyl]-3-(imidazol-1-yl)-1-propene was used instead of 2-[2-(2,4-dichlorobenzyloxy)phenyl]-3-(imidazol-1-yl)-1-propene.

EXAMPLE 33

2-[2-(2,6-Dichlorobenzyloxy)-5-fluorophenyl]-3-(imidazol-1-yl)-1-propene oxalate According to the same manner as in Example 28, the title compound (m.p. 118°–121° C.) was obtained except that 2-[2-(2,6-dichlorobenzyloxy)-5-fluorophenyl]-3-(imidazol-1-yl)-1-propene was used instead of 2-[2-(2,4-dichlorobenzyloxy)phenyl]-3-(imidazol-1-yl)-1-propene.

EXAMPLE 34

2-[2-(2,4-Dichlorobenzyloxy)phenyl]-3-(1,2,4-triazol-1-yl)-1-propene oxalate

ω-(1,2,4-Triazol-1-yl)-2-(2,4-dichlorobenzyloxy)acetophenone (0.70 g, 1.93 mmole), potassium carbonate (0.36 g, 2.60 mmole) and methyltriphenylphosphonium bromide (0.79 g, 2.21 mmole) were suspended in 1,4-dioxane (15 ml) and the mixture was refluxed with stirring for 2 days. Then, according to the same manner as in Example 25, 2-[2-(2,4-dichlorobenzyloxy)phenyl]-3-(1,2,4-triazol-1-yl)-1-propene was obtained. Further, according to the same manner as in Example 28, the title compound (0.16 g, 18.4%) was obtained, m.p. 130°–131° C. (recrystallized from methanol/diethyl ether).

Anal. Calcd. for $C_{20}H_{17}Cl_2N_3O_5$: C, 53.10; H, 3.81; N, 9.33. Found: C, 53.10; H, 3.84; N, 9.30.

EXAMPLE 35

2-[2-(2,4-Dichlorobenzyloxy)-5-methylphenyl]-3-(imidazol-1-yl)-1-propene oxalate According to the same manner as in Example 34, the title compound (m.p. 139°–141° C.) was obtained except that ω-(imidazol-1-yl)-2-(2,4-dichlorobenzyloxy)-5-methylacetophenone was used instead of ω-(1,2,4-triazol-1-yl)-2-(2,4-dichlorobenzyloxy)acetophenone.

EXAMPLE 36

2-[2-(2,4-Dichlorobenzyloxy)-5-chlorophenyl]-3-(imidazol-1-yl)-1-propene oxalate According to the same manner as in Example 34, the title compound (m.p. 159°–161° C.) was obtained except that ω-(imidazol-1-yl)-2-(2,4-dichlorobenzyloxy)-5-chloroacetophenone was used instead of ω-(1,2,4-tirazol-1-yl)-2-(2,4-dichlorobenzyloxy)acetophenone.

EXAMPLE 37

2-(2-Hydroxyphenyl)-3-(imidazol-1-yl)-1-propene

1-Propene (9.0 g, 25.1 mmole) was dissolved in anisole (45 ml) and anhydrous aluminum chloride (8.33 g, 62.5 mmole) was added to the solution with stirring and ice-cooling. After stirring for additional 1 hour with ice-cooling, an aqueous saturated solution of sodium bicarbonate (300 ml) was added and the mixture was extracted with ethyl acetate (300 ml×2). The extract was washed with an aqueous saturated sodium chloride solution (200 ml) and dried over anhydrous sodium sulfate. After distilling off the solvent under reduced pressure, the residue was subjected to chromatography on a silica gel column and eluted with methylene chloride/methanol to obtain the title compound (0.69 g, 13.8%), m.p. 139°–141° C. (recrystallized from ethyl acetate).

Anal. Calcd. for $C_{12}H_{12}N_2O$: C, 71.98; H, 6.04; N, 13.99. Found: C, 71.46; H, 6.03; N, 13.82.

EXAMPLE 38

2-[2-(4-Phenylbenzyloxy)phenyl]-3-(imidazol-1-yl)propene 2-(2-Hydroxyphenyl)-3-(imidazol-1-yl)-1-propene (400 mg, 2.0 mmole) was dissolved in dimethylformamide (5 ml) and sodium hydride (60% dispersion in oil)(110 mg, 2.75 mmole) was added to the solution with stirring and ice-cooling. After stirring for additional 30 minutes, 4-phenylbenzylchloride (490 mg, 2.42 mmole) was added and the mixture was stirred overnight at room temperature. Then, the mixture was poured into water (50 ml) and extracted with diethyl ether (75 ml×2). The extract was washed with water (50 ml×2) and dried over anhydrous sodium sulfate. After distilling off the solvent, the residue was subjected to chromatography on a silica gel column and eluted with methylene chloride/methanol to obtain the title compound (0.41 g, 55.9%), m.p. 90°-92° C. (recrystallized from ethyl acetate/n-hexane).

Anal. Calcd. for $C_{25}H_{22}N_2O$: C, 81.94; H, 6.05; N, 7.65. Found: C, 81.98; H, 5.92; N, 7.49.

EXAMPLES 39 TO 71

According to the above-described manner, the following compounds of the present invention were prepared.

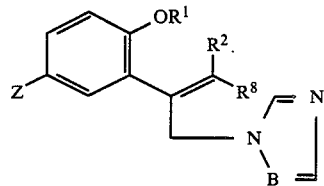

| Example No. | $R^1$ | $R^2$ | $R^3$ | Z | B | Salt | m.p. (°C.) |
|---|---|---|---|---|---|---|---|
| 39 | —CH₂—C₆H₅ | H | H | H | CH | — | $n_D^{20.0}$ = 1.5947 |
| 40 | —CH₂—C₆H₅ | H | H | CH₃ | CH | — | 76–77 |
| 41 | —CH₂—C₆H₅ | H | H | F | CH | (CO₂H)₂ | 124.5–126 |
| 42 | —CH₂—C₆H₅ | H | H | Cl | CH | (CO₂H)₂ | 128–130 |
| 43 | —CH₂C(O)—C₆H₅ | H | H | H | CH | — | 77–80 |
| 44 | —CH(CH₃)₂ | H | H | H | CH | (CO₂H)₂ | 112–114 |
| 45 | —(CH₂)₃CH₃ | H | H | H | CH | — | $n_D^{19.9}$ = 1.5498 |
| 46 | —CH₂—(2,4-Cl₂C₆H₃) | H | H | H | CH | — | 126–127 |
| 47 | —(CH₂)₂—O—C₆H₅ | H | H | H | CH | (CO₂H)₂ | 141–143 |
| 48 | —CH(CH₃)—C₆H₅ | H | H | H | CH | (CO₂H)₂ | 111–113 |
| 49 | —(CH₂)₂—C₆H₅ | H | H | H | CH | (CO₂H)₂ | 125–127 |
| 50 | —(CH₂)₂CH₃ | H | H | H | CH | (CO₂H)₂ | 88–89 |
| 51 | —CH₂CH=CH₃ | H | H | H | CH | (CO₂H)₂ | 87–88 |
| 52 | —CH₂CH=CH₂ | H | H | F | CH | (CO₂H)₂ | 85–86.5 |
| 53 | —CH₂CH=CH₂ | H | H | Cl | CH | (CO₂H)₂ | 101–103 |
| 54 | —CH₂C≡CH | H | H | H | CH | (CO₂H)₂ | 121–123 |
| 55 | —CH₂C≡CH | H | H | F | CH | (CO₂H)₂ | 118–118.5 |
| 56 | —CH₂C≡CH | H | H | Cl | CH | (CO₂H)₂ | 125–126 |
| 57 | —(CH₂)₄ | H | H | H | CH | (CO₂H)₂ | 117–118 |
| 58 | —(CH₂)₆ | H | H | H | CH | (CO₂H)₂ | 85–86 |
| 59 | —CH₂C(O)—N(CH₃)—C₆H₅ | H | H | H | CH | (CO₂H).H₂O | 156–158 |
| 60 | —(CH₂)₇CH₃ | H | H | H | CH | (CO₂H)₂ | 87–89 |
| 61 | —(CH₂)₇CH₃ | H | H | CH₃ | CH | (CO₂H)₂.2/1H₂O | 92–94 |
| 62 | —(CH₂)₇CH₃ | H | H | Cl | CH | (CO₂H)₂ | 114–115 |
| 63 | —(CH₂)₉CH₃ | H | H | H | CH | (CO₂H)₂ | 104–106 |

-continued

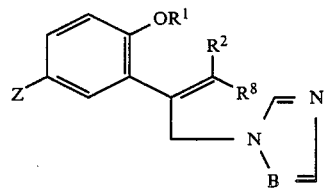

| Example No. | R¹ | R² | R³ | Z | B | Salt | m.p. (°C.) |
|---|---|---|---|---|---|---|---|
| 64 | -CH₂-(2,3-Cl₂-C₆H₃) | H | H | H | CH | $(CO_2H)_2$ | 98–99 |
| 65 | -CH₂-(2,4-Cl₂-C₆H₃) | H | H | F | CH | $(CO_2H)_2$ | 126–128 |
| 66 | -CH₂-(2,4-Cl₂-C₆H₃) | H | H | Cl | CH | — | 109–110 |
| 67 | -CH₂-(4-Cl-C₆H₄) | H | H | H | CH | $(CO_2H)_2$ | 108–109 |
| 68 | -CH₂-(3-Cl-C₆H₄) | H | H | H | CH | $(CO_2H)_2$ | 97–99 |
| 69 | -CH₂-(3-Cl-C₆H₄) | H | H | CH₃ | CH | $(CO_2H)_2$ | 101–102 |
| 70 | -CH₂-(3-Cl-C₆H₄) | H | H | F | CH | $(CO_2H)_2$ | 119–120 |
| 71 | -CH₂-(3-Cl-C₆H₄) | H | H | Cl | CH | $(CO_2H)_2$ | 113–114 |

EXAMPLE 72

3-[2-(2,4-Dichlorobenzyloxy-5-fluoro)phenyl]-4-(imidazol-1-yl)-2-butene.5/4 oxalate ω-(Imidazol-1-yl)-2-(2,4-dichlorobenzyloxy)-5-fluoroactophenone (0.76 g, 2.0 mmole), potassium carbonate (0.44 g, 3.18 mmole) and ethyltripheneylphospohnium bromide (1.11 g, 2.99 mmole) were suspended in 1,4-dioxane 16 ml and the suspension was heated under reflux for 12 hours. Then, according to the same manner as in Example 34, the title compound (0.80 g, 79.4%) was obtained, m.p. 158°–160° C. (recrystallized from methanol/diethyl ether).

Anal. Calcd. for $C_{20}H_{17}Cl_2FN_2O.5/4C_2H_2O_4$: C, 53.63; H, 3.99; N, 5.56. Found: C, 53.92; H, 4.06; N, 5.63.

EXAMPLE 73

3-[2-(2,4-Dichlorobenzyloxy)phenyl]-4-(imidazol-1-yl)-2-butene.3/2 oxalate

According to the same manner as in Example 72, the title compound (m.p. 113°–115° C.) was obtained except that ω-(imidazol-1-yl)-2-(2,4-dichlorobenzyloxy)acetophenone was used instead of ω-(imidazol-1-yl)-2-(2,4-dichlorobenzyloxy)-5-fluoroacetophenone.

EXAMPLE 74

2-[2-(2,4-Dichlorobenzyloxy)phenyl]-3-(1,2,4-triazol-1-yl)-1-propene 1,2,4-Triazole (59 mg, 0.854 mmole) and potassium carbonate (129 mg, 0.933 mmole) were suspended in dimethylformamide (1 ml) and a solution of 2-[2-(2,4-dichlorobenzyloxy)phenyl]-3-bromo-1-propene (290 mg, 0.779 mmole) in dimethylformamide (2 ml) was added dropwise to the suspension. Then, after stirring overnight at room temperature, the reaction mixture was worked up according to the same manner as in Example 25 to obtain the title compound (0.20 g, 71.2%). By comparing ¹H-NMR and Rf value of TLC of the resulting compound with those of the product of the alternative process described in Example 34, it was confirmed that both chemical structures were identical with each other.

REFERENCE EXAMPLE 3

2-(2,4-Dichlorobenzyloxy)acetophenone o-Hydroxyacetophenone (40.85 g, 300 mmole) was dissolved in dimethyl sulfoxide (150 ml) and potassium carbonate (49.0 g, 355 mmole) was added to the mixture. Then, 2,4-dichlorobenzyl chloride (65.9 g, 337 mmole) was added dropwise with stirring. Stirring was continued at room temperature for 24 hours and water (225 ml) was added dropwise over 1 hour. After stirring at room temperature for additional 1 hour, the precipitated crystals were filtered off, washed with water (200 ml×3) and recrystallized from methanol to obtain the title compound (82.7 g, 93.4%), m.p. 83°–85° C.

REFERENCE EXAMPLE 4

ω-Bromo-2-(2,4-dichlorobenzyloxy)acetophenone 2-(2,4-Dichlorobenzyloxy)acetophenone (29.52 g, 100 mmole) was dissolved in a mixture of diethyl ether (100 ml) and 1,4-dioxane (100 mmole) and bromine (16 g, 100 mmole) was added dropwise over 1 hour. After stirring at the same temperature for additional 1 hour, water (200 ml) was added and the mixture was separated into layers. The aqueous layer was extracted with diethyl ether (200 ml). The organic layers were combined, washed with 1% aqueous solution of sodium bicarbonate (180 ml) and dired over anhydrous sodium sulfate. The solvent was distilled off under reduced pressure and a mixture of benzene/n-hexane was added to the residue to crystallize. The crystals were filtered off to obtain a crude product of the title compound (28.57 g). The crude product (1 g, 2.67 mmole) was recrystallized from benzene/n-hexane to obtain the title compoud (0.79 g, 79%), m.p. 89°–91° C.

Anal. Calcd. for $C_{15}H_{11}BrCl_2$: C, 48.16; H, 2.97. Found: C, 47.65; H, 2.97.

REFERENCE EXAMPLE 5

ω-(Imidazol-1-yl)-2-(2,4-dichlorobenzyloxy)acetophenone

1H-Imidazole (10.21 g, 150 mmole) was dissolved in dimethylformamide (20 ml) and ω-bromo-2-(2,4-dichlorobenzyloxy)acetophenone (11.2 g, 29.9 mmole) was added slowly. After stirring for 2.5 hours with ice-cooling, water (120 ml) was added and the mixture was extracted with ethyl acetate (120 ml×2). The extract was washed with water (120 ml×2) and dried over anhydrous sodium sulfate. After distilling off the solvent under reduced pressure, the residue was subjected to chromatography on a silica gel columne and eluted with methanol/chloroform to obtain the title compound (8.37 g, 77.2%), m.p. 109°–111° C. (recrystallized from n-hexane/benzene).

Anal. Calcd. for $C_{18}H_{14}Cl_2N_2O_2$: C, 59.84; H, 3.91; N, 7.76. Found: C, 59.68; H, 4.01; N, 7.66.

REFERENCE EXAMPLE 6

2-[2-(2,4-Dichlorobenzyloxy)phenyl]-1-propene

Under argon atmosphere, methylmagnesium bromide (14 ml, 3 mole/l diethyl ether solution; methylmagnesium bromide 42 mmole) was added dropwise over 10 minutes to a solution of 2-(2,4-dichlorobenzyloxy)acetopheneone (5.0 g, 16.9 mmole) in tetrahydrofuran dried with molecular sieve (40 ml), while maintaining the inner temperature at 10° to 20° C. After stirring at room temperature for 2 hours, the mixture was poured into water 100 ml. The mixture was adjusted to pH 7 with 6N hydrochloric acid and extracted with ethyl acetate (100 ml×2). The extract was washed with water (75 ml×2) and dried over anhydrous sodium sulfate. The solvent was distilled off under reduced pressure to obtain an oily residue. The residue was dissolved in benzene (40 ml) and p-toluenesulfonic acid monohydrate (0.33 g, 1.73 mmole) was added to the solution. The mixture was refluxed with stirring for 1 hour. Then, the mixture was poured into water (50 ml) and extracted with benzene (50 ml×2). The extract was washed with water (50 ml) and dried over anhydrous sodium sulfate. After distilling off the solvent, the residue was subjected to chromatography on a silica gel column and eluted with n-hexane to obtain the title compound (2.54 g, 51.1%). $n^{19.6} = 1.5831$; $^1$H-NMR(CDCl$_3$, δ): 2.17 (s, 3H, CH$_3$), 5.00–5.27 (m, 4H, >C=CH$_2$,

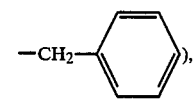

6.77–7.70 (m, 7H, aromatic).

REFERENCE EXAMPLE 7

2-[2-(2,4-Dichlorobenzyloxy)phenyl]-3-bromo-1-propene

2-[2-(2,4-Dichlorobenzyloxy)phenyl]-1-propene (1.0 g, 3.41 mmole), N-bromosuccinimide (0.61 g, 3.41 mmole) and azobisisobutyronitrile (2.8 mg, 0.017 mmole) were suspended in carbon tetrachloride (4 ml) and the suspension was refluxed with stirring for 12 hours. Then, the mixture was poured into water (30 ml) and extracted with ethyl acetate (50 ml). The extract was washed with water (50 ml) and dried over anhydrous soidum sulfate. After distilling off the solvent under reduced pressure, the residue was subjected to chromatography on a silica gel column and eluted with n-hexane to obtain the title compound (0.52 g, 41.0%). $^1$H-NMR (CDCl$_3$, δ): 4.50 (s, 2H, CH$_2$Br), 5.20 (s, 2H,

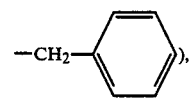

5.33 (d, 1H, =CH), 5.57 (d, 1H, =CH), 6.80–7.57 (m, 7H, aromatic).

REFERENCE EXAMPLES 8 TO 23

According to the same manner as in Reference Examples 3 to 5, the following substituted acetophenones were prepared.

Structure:

2-OR¹, 5-Z substituted phenyl with -C(=O)-CH₂-Y group

| Reference Example | R¹ | Y | Z | m.p. (°C.) |
|---|---|---|---|---|
| 8 | -CH₂-(2,4-dichlorophenyl) | H | H | 83–85 |
| 9 | -CH₂-(2,4-dichlorophenyl) | Br | H | 89–91 |
| 10 | -CH₂-(2,4-dichlorophenyl) | -N(imidazol-1-yl) | H | 109–111 |
| 11 | -CH₂-(2,4-dichlorophenyl) | -N(1,2,4-triazol-1-yl) | H | 130–131.5 |
| 12 | -CH₂-(2,4-dichlorophenyl) | H | F | 97–98 |
| 13 | -CH₂-(2,4-dichlorophenyl) | Br | F | 98–101 |
| 14 | -CH₂-(2,4-dichlorophenyl) | -N(imidazol-1-yl) | F | 121–122 |
| 15 | -CH₂-(2,4-dichlorophenyl) | H | Cl | 104–105 |
| 16 | -CH₂-(2,4-dichlorophenyl) | Br | Cl | 98–101 |
| 17 | -CH₂-(2,4-dichlorophenyl) | -N(imidazol-1-yl) | Cl | 99–100 |
| 18 | -CH₂-(2,4-dichlorophenyl) | H | CH₃ | 82–86 |
| 19 | -CH₂-(2,4-dichlorophenyl) | Br | CH₃ | 125–127 |
| 20 | -CH₂-(2,4-dichlorophenyl) | -N(imidazol-1-yl) | CH₃ | 133–135 |
| 21 | -CH₂-(2,6-dichlorophenyl) | H | F | —* |
| 22 | -CH₂-(2,6-dichlorophenyl) | Br | F | —* |
| 23 | -CH₂-(2,6-dichlorophenyl) | -N(imidazol-1-yl) | F | 132–135 |

*The compound was used in the next step without purification.

REFERENCE EXAMPLE 24

According to the same manner as in Reference Example 2, 2-hydroxy-5-chloroacetophenone was prepared, b.p. 98° C./15 mmHg.

REFERENCE EXAMPLE 25

According to the same manner as in Reference Example 2, 2-hydroxy-5-methylacetophenone was prepared, m.p. 45°–46.5° C.

In order to show fungicidal activity of the compounds of the present invention, effect on preventing and suppressing of grey mold diseases and powdery mildew were tested.

Experiment 1

Test for controlling grey mold diseases of cucumber.

Prevention test

A solution (12 ml) containing a compound to be tested in a predetermined concentration was sprinkled on the first leaf of a single planting soil culture plantlet of cucumber (variety: Tsukuba Shiroibo) in a plastic cup having 9 cm in diameter in a greenhouse, and then air-dried. After 24 hours, spores or a mat of hyphae of Botrytis cinerea were inoculated, and cucumber was kept for 2 to 4 days under conditions of temperature of $20° \pm 2°$ C. and humidity of 90 to 100%. Then, the diameter of a disease spot formed was measured and the rate of prevention was calculated from the following formula. The result are shown in Table 1.

$$\text{Rate of Prevention} = \frac{\text{Diameter of spot of non-treated control group} - \text{Diameter of spot of a group treated with a test compound}}{\text{Diameter of spot of non-treated control group}} \times 100(\%)$$

Suppression test

A mat of hyphae of Botrytis cinerea was inoculated on the first leaf of a single planting soil culture plantlet of cucumber (variety: Tsukuba Shiroibo) in a plastic cup having 9 cm in diameter in a greenhouse to slightly cause disease (after about 1 day). Then, a solution (12 ml) containing a compound to be tested in a predetermined concentration was sprinkled and cucumber was kept for 48 hours under conditions of temperature of $20° \pm 2°$ C. and humidity of 90 to 100%. The rate of prevention was calculated as described above.

Experiment 2

Test for controlling powdery mildew of cucumber.

Prevention test

A solution (12 ml) containing a compound to be tested in a predetermined concentration was sprinkled on the first leaf of a single planting soil culture plantlet of cucumber (variety: Tsukuba Shiroibo) in a plastic cup having 9 cm in diameter in a greenhouse, and air-dried. After 24 hours, a suspension of spores of Sphaerotheca fuliginea was inoculated and cucumber was kept for 14 days under conditions of temperature of $25° \pm 2°$ C. and humidity of about 50%. The result was evaluated according to the prevention index which is corresponding to the following sign appearing rate to determine the prevention rate. The results are shown in Table 1.

| Prevention index | Prevention rate (%) | Criteria |
| --- | --- | --- |
| 0 | 0 | Sign is observed throughout the leaf. |
| 3 | 50 | Sign is observed on over 50% area of the leaf. |
| 5 | 70 | Sign is observed on about 30% to 50% area of the leaf. |
| 7 | 90 | Sign is observed on about 10% to 30% area of leaf. |
| 9 | 97 | Sign is slightly observed. |
| 10 | 100 | No sign is observed. |

Suppression test

A suspension of spores of Sphaerotheca fuliginea was inoculated on the first leaf of a single planting soil culture plantlet of cucumber (variety: Tsukuba Shiroibo) in a plastic cup having 9 cm in diameter in a greenhouse to slightly cause disease (after about 2 days). Then, a solution (12 ml) containing a compound to be tested in a predetermined concentration was sprinkled and cucumber was kept for 12 days under conditions of temperature of $25° \pm 2°$ C. and humidity of about 50%. The rate of prevention was determined as described above. The results are shown in Table 1.

TABLE 1

| Compound (Ex. No.) | Conc. (ppm) | Control rate (%) Botrytis cinerea | | Sphaerotheca fuliginea | |
| --- | --- | --- | --- | --- | --- |
| | | Prevention test | Treatment test | Prevention test | Treatment test |
| 2 | 500 | 100 | — | 100 | — |
| | 125 | 90 | 46 | 100 | 100 |
| | 31.3 | 68 | 45 | 90 | 97 |
| | 7.8 | 49 | 38 | 70 | 95 |
| | 2.0 | 12 | 15 | 10 | 40 |
| | 0.5 | — | — | 0 | 0 |
| 3 | 500 | 70 | — | 100 | — |
| | 125 | 81 | 88 | 99 | 100 |
| | 31.3 | 66 | 80 | 95 | 100 |
| | 7.8 | 41 | 61 | 30 | 90 |
| | 2.0 | 3 | 20 | 0 | 30 |
| | 0.5 | — | — | 0 | 0 |
| 4 | 500 | 0 | — | 100 | — |
| | 125 | — | — | 90 | 100 |
| | 31.3 | — | — | 60 | 95 |
| | 7.8 | — | — | 0 | 30 |
| | 2.0 | — | — | 0 | 0 |
| | 0.5 | — | — | 0 | 0 |
| 5 | 500 | 70 | — | 100 | — |
| | 125 | 72 | 95 | 90 | 100 |
| | 31.3 | 39 | 84 | 70 | 95 |
| | 7.8 | 9 | 51 | 20 | 70 |
| | 2.0 | 1 | 9 | 0 | 20 |
| | 0.5 | — | — | 0 | 0 |
| 6 | 500 | 60 | 83 | 100 | — |
| | 125 | 29 | 56 | 100 | 100 |
| | 31.3 | 8 | 10 | 90 | 70 |
| | 7.8 | — | 3 | 10 | 30 |
| | 2.0 | — | — | 0 | 0 |
| | 0.5 | — | — | — | — |
| 7 | 500 | 0 | — | 100 | — |
| | 125 | — | — | 95 | 100 |
| | 31.3 | — | — | 90 | 95 |
| | 7.8 | — | — | 20 | 80 |
| | 2.0 | — | — | 0 | 20 |
| | 0.5 | — | — | 0 | 0 |
| 8 | 500 | 35 | — | — | — |
| | 125 | — | — | 100 | 100 |
| | 31.3 | — | — | 100 | 100 |
| | 7.8 | — | — | 80 | 70 |
| | 2.0 | — | — | 10 | 20 |
| | 0.5 | — | — | 0 | 0 |
| 9 | 500 | 30 | — | — | — |
| | 125 | — | — | 100 | 100 |
| | 31.3 | — | — | 100 | 100 |
| | 7.8 | — | — | 60 | 80 |
| | 2.0 | — | — | 20 | 30 |

TABLE 1-continued

| Compound (Ex. No.) | Conc. (ppm) | Control rate (%) Botrytis cinerea Prevention test | Control rate (%) Botrytis cinerea Treatment test | Sphaerotheca fuliginea Prevention test | Sphaerotheca fuliginea Treatment test |
|---|---|---|---|---|---|
| | 0.5 | — | — | 0 | 0 |
| 14 | 500 | 0 | — | 100 | — |
| | 125 | — | — | 100 | 100 |
| | 31.3 | — | — | 90 | 99 |
| | 7.8 | — | — | 40 | 85 |
| | 2.0 | — | — | 0 | 10 |
| | 0.5 | — | — | — | — |
| 15 | 500 | 20 | — | 100 | — |
| | 125 | — | — | 100 | 100 |
| | 31.3 | — | — | 95 | 95 |
| | 7.8 | — | — | 30 | 30 |
| | 2.0 | — | — | 0 | 0 |
| | 0.5 | — | — | — | — |
| 17 | 500 | 40 | — | 100 | — |
| | 125 | — | — | 100 | 100 |
| | 31.3 | — | — | 90 | 95 |
| | 7.8 | — | — | 10 | 20 |
| | 2.0 | — | — | 0 | 0 |
| | 0.5 | — | — | 0 | 0 |
| 18 | 500 | 83 | 41 | 100 | 100 |
| | 125 | 46 | 33 | 100 | 100 |
| | 31.3 | 17 | 16 | 90 | 80 |
| | 7.8 | 13 | 0 | 10 | 20 |
| | 2.0 | 0 | 0 | 0 | 0 |
| | 0.5 | — | — | — | — |
| 19 | 500 | 40 | — | 100 | — |
| | 125 | — | — | 100 | 100 |
| | 31.3 | — | — | 100 | 100 |
| | 7.8 | — | — | 50 | 90 |
| | 2.0 | — | — | 10 | 30 |
| | 0.5 | — | — | — | — |
| 20 | 500 | 25 | — | 100 | — |
| | 125 | — | — | 100 | 100 |
| | 31.3 | — | — | 50 | 90 |
| | 7.8 | — | — | 0 | 20 |
| | 2.0 | — | — | 0 | 0 |
| | 0.5 | — | — | — | — |
| 22 | 500 | 100 | 86 | 100 | — |
| | 125 | 61 | 71 | 95 | 100 |
| | 31.3 | 32 | 35 | 20 | 50 |
| | 7.8 | 9 | 8 | 0 | 0 |
| | 2.0 | — | — | 0 | 0 |
| | 0.5 | — | — | — | — |
| 23 | 500 | 0 | — | 100 | — |
| | 125 | — | — | 100 | 100 |
| | 31.3 | — | — | 90 | 100 |
| | 7.8 | — | — | 50 | 90 |
| | 2.0 | — | — | 0 | 10 |
| | 0.5 | — | — | 0 | 0 |
| 24 | 500 | 10 | — | 100 | — |
| | 125 | — | — | 30 | 30 |
| | 31.3 | — | — | 0 | 10 |
| | 7.8 | — | — | 0 | 0 |
| | 2.0 | — | — | 0 | 0 |
| | 0.5 | — | — | — | — |
| 25 | 500 | 70 | — | 100 | — |
| | 125 | — | — | 100 | 100 |
| | 31.3 | — | — | 100 | 100 |
| | 7.8 | — | — | 100 | 100 |
| | 2.0 | — | — | 90 | 95 |
| | 0.5 | — | — | 10 | 20 |
| 27 | 500 | 0 | — | 100 | — |
| | 125 | — | — | 100 | 100 |
| | 31.3 | — | — | 100 | 100 |
| | 7.8 | — | — | 95 | 97 |
| | 2.0 | — | — | 70 | 90 |
| | 0.5 | — | — | 10 | 10 |
| 28 | 500 | 50 | — | 100 | — |
| | 125 | — | — | 100 | 100 |
| | 31.3 | — | — | 100 | 100 |
| | 7.8 | — | — | 80 | 100 |
| | 2.0 | — | — | 40 | 90 |
| | 0.5 | — | — | 0 | 60 |
| 32 | 500 | 100 | 90 | — | — |
| | 125 | 73 | 85 | 100 | 100 |
| | 31.3 | 63 | 65 | 100 | 100 |
| | 7.8 | 23 | 32 | 95 | 100 |
| | 2.0 | 3 | 3 | 40 | 80 |
| | 0.5 | — | — | 10 | 30 |
| 33 | 500 | 90 | 95 | 100 | — |
| | 125 | 100 | 90 | 100 | 100 |
| | 31.3 | 100 | 72 | 100 | 100 |
| | 7.8 | 30 | 50 | 95 | 100 |
| | 2.0 | 0 | 6 | 50 | 95 |
| | 0.5 | — | — | 0 | 50 |
| 34 | 500 | 57 | — | 100 | — |
| | 125 | — | — | 100 | 100 |
| | 31.3 | — | — | 90 | 100 |
| | 7.8 | — | — | 50 | 100 |
| | 2.0 | — | — | 0 | 80 |
| | 0.5 | — | — | — | 40 |
| 35 | 500 | 81 | — | 100 | — |
| | 125 | — | — | 100 | 100 |
| | 31.3 | — | — | 100 | 100 |
| | 7.8 | — | — | 100 | 95 |
| | 2.0 | — | — | 40 | 95 |
| | 0.5 | — | — | 0 | 80 |
| 37 | 500 | 0 | — | 100 | — |
| | 125 | — | — | 100 | 100 |
| | 31.3 | — | — | 70 | 99 |
| | 7.8 | — | — | 10 | 30 |
| | 2.0 | — | — | 0 | 0 |
| | 0.5 | — | — | — | — |
| 38 | 500 | 90 | 77 | 100 | — |
| | 125 | 73 | 64 | 100 | 100 |
| | 31.3 | 51 | 47 | 100 | 100 |
| | 7.8 | 21 | 24 | 70 | 95 |
| | 2.0 | 3 | 5 | 10 | 40 |
| | 0.5 | — | — | 0 | 0 |
| 39 | 500 | 0 | — | 100 | — |
| | 125 | — | — | 70 | 95 |
| | 31.3 | — | — | 30 | 70 |
| | 7.8 | — | — | 0 | 10 |
| | 2.0 | — | — | 0 | 0 |
| | 0.5 | — | — | — | — |
| 45 | 500 | 70 | — | 100 | — |
| | 125 | — | — | 99 | 100 |
| | 31.3 | — | — | 70 | 100 |
| | 7.8 | — | — | 10 | 90 |
| | 2.0 | — | — | 0 | 20 |
| | 0.5 | — | — | 0 | 0 |
| 47 | 500 | 50 | — | 100 | — |
| | 125 | — | — | 80 | 95 |
| | 31.3 | — | — | 40 | 70 |
| | 7.8 | — | — | 0 | 10 |
| | 2.0 | — | — | 0 | 0 |
| | 0.5 | — | — | — | — |
| 49 | 500 | 50 | — | 100 | — |
| | 125 | — | — | 80 | 95 |
| | 31.3 | — | — | 70 | 85 |
| | 7.8 | — | — | 10 | 20 |
| | 2.0 | — | — | 0 | 0 |
| | 0.5 | — | — | — | — |
| 50 | 500 | 0 | — | 100 | — |
| | 125 | — | — | 90 | 97 |
| | 31.3 | — | — | 30 | 60 |
| | 7.8 | — | — | 0 | 10 |
| | 2.0 | — | — | 0 | 0 |
| | 0.5 | — | — | — | — |
| 51 | 500 | 0 | — | 100 | — |
| | 125 | — | — | 85 | 95 |
| | 31.3 | — | — | 50 | 40 |
| | 7.8 | — | — | 0 | 10 |
| | 2.0 | — | — | 0 | 0 |
| | 0.5 | — | — | — | — |
| 54 | 500 | 0 | — | 100 | — |
| | 125 | — | — | 80 | 95 |
| | 31.3 | — | — | 30 | 70 |
| | 7.8 | — | — | 0 | 10 |
| | 2.0 | — | — | 0 | 0 |
| | 0.5 | — | — | — | — |
| 57 | 500 | 70 | 88 | 100 | — |

TABLE 1-continued

| Compound (Ex. No.) | Conc. (ppm) | Control rate (%) Botrytis cinerea | | Sphaerotheca fuliginea | |
|---|---|---|---|---|---|
| | | Prevention test | Treatment test | Prevention test | Treatment test |
| | 125 | 90 | 75 | 100 | 100 |
| | 31.3 | 59 | 59 | 97 | 99 |
| | 7.8 | 12 | 18 | 30 | 70 |
| | 2.0 | 0 | 0 | 0 | 10 |
| | 0.5 | — | — | 0 | 0 |
| 58 | 500 | 0 | — | 100 | — |
| | 125 | — | — | 100 | 100 |
| | 31.3 | — | — | 100 | 100 |
| | 7.8 | — | — | 40 | 90 |
| | 2.0 | — | — | 0 | 20 |
| | 0.5 | — | — | 0 | 0 |
| 60 | 500 | 50 | 73 | 100 | — |
| | 125 | 61 | 63 | 100 | 100 |
| | 31.3 | 33 | 37 | 97 | 100 |
| | 7.8 | 4 | 14 | 10 | 90 |
| | 2.0 | 0 | 0 | 0 | 30 |
| | 0.5 | — | — | 0 | 0 |
| 63 | 500 | 0 | — | 100 | — |
| | 125 | — | — | 99 | 100 |
| | 31.3 | — | — | 97 | 100 |
| | 7.8 | — | — | 40 | 95 |
| | 2.0 | — | — | 0 | 40 |
| | 0.5 | — | — | 0 | 0 |
| 72 | 500 | 90 | 83 | 100 | — |
| | 125 | 69 | 68 | 100 | 100 |
| | 31.3 | 47 | 35 | 100 | 100 |
| | 7.8 | 10 | 2 | 90 | 99 |
| | 2.0 | 3 | 0 | 20 | 70 |
| | 0.5 | — | — | 0 | 10 |
| 73 | 500 | 90 | 86 | 100 | — |
| | 125 | 72 | 69 | 100 | 100 |
| | 31.3 | 40 | 37 | 100 | 100 |
| | 7.8 | 10 | 2 | 85 | 97 |
| | 2.0 | 2 | 0 | 10 | 50 |
| | 0.5 | — | — | 0 | 10 |

The following Preparations illustrate examples of the formulation of the fungicidal preparation of the present invention. In Preparation, all "parts" are by weight.

Preparation 1

The compound of the present invention (5 parts), propylene alcohol (20 parts), polyoxyethylene alkylphenyl ether (5 parts) and water (70 parts) are admixed to obtain an aqueous solution.

The solution is diluted so that the concentration of the compound of the present invention is 10 to 500 ppm and is sprinkled on leaves and stems.

Preparation 2

The compound of the present invention (50 parts), sodium alkylbenzene sulfonate (6 parts), sodium lignin sulfonate (4 parts) and clay (40 parts) are admixed and pulverized to obtain a wettable powdery preparation.

This preparation is diluted so that the concentration of the compound of the present invention is 10 to 500 ppm and is sprinkled on fruits.

Preparation 3

The compound of the present invention (5 parts), a mixture of equal amounts of bentonite and talc (90 parts) and sodium alkylbenzene sulfonate (5 parts) are admixed and pulverized. Then, the mixture is granulated to obtain a granular preparation.

Preparation 4

The compound of the present invention (25 parts), polyoxyethylene alkylphenyl ether (8 parts), sodium alkylbenzene sulfonate (2 parts) and xylene (65 parts) are admixed and emulsified to obtain an emulsion.

This emulsion is diluted so that the concentration of the compound of the present invention is 50 to 500 ppm and is sprinkled on leaves and stems.

Preparation 5

The compound of the present invention (1 part) and talc (99 parts) are admixed to obtain a powdery preparation.

What is claimed is:

1. A compound of the formula:

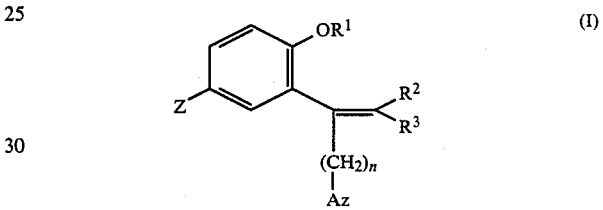
(I)

wherein $R^1$ is hydrogen, alkyl having 1 to 12 carbon atoms,

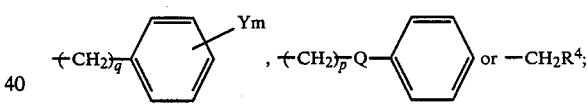

$R^2$ and $R^3$ are hydrogen, bromine or methyl; $R^4$ is alkenyl having 2 to 9 carbon atoms or alkynyl having 2 to 9 carbon atoms; m is an integer of 0 to 2; n is an integer of 0 to 1; p and q are independently integers of 1 to 8; Az is imidazol-1-yl or 1,2,4-triazol-1-yl, Q is —CO—, —O— or —CO—NR$^5$—; $R^5$ is hydrogen or methyl; Y is hydrogen, fluorine, chlorine or phenyl; and Z is hydrogen, fluorine, chlorine or methyl, provided that, when Z is hydrogen, methyl or chlorine, n is 1 or its salt.

2. The compound 1-[1-[2-(2,6-dichlorobenzyloxy)-5-fluorophenyl]vinyl]-1H-imidazole.

3. A fungicidal composition which comprises as an effective ingredient the compound of the formula (I) as claimed in claim 1 and one or more carriers.

* * * * *